United States Patent [19]

Shore et al.

[11] Patent Number: 4,496,532

[45] Date of Patent: Jan. 29, 1985

[54] RUTHENIUM CARBONYLATES AND PROCESSES FOR THEIR PREPARATION

[75] Inventors: Sheldon G. Shore; Alakananda Bhattacharyya, both of Columbus, Ohio

[73] Assignee: The Ohio State University Research Foundation, Columbus, Ohio

[21] Appl. No.: 517,723

[22] Filed: Jul. 27, 1983

[51] Int. Cl.$^3$ .................. C01G 1/04; C01G 55/00; C07F 15/00

[52] U.S. Cl. .................. 423/417; 423/418; 260/429 R

[58] Field of Search .................. 423/416–418; 260/429 R

[56] References Cited

U.S. PATENT DOCUMENTS 4,349,521 9/1982 Shore et al. .................. 423/417

OTHER PUBLICATIONS

Shore, Sheldon G. and Nagel, Colleen C., J.C.S. Chem. Comm., 1980, 530.

*Primary Examiner*—Earl C. Thomas
*Attorney, Agent, or Firm*—Sidney W. Millard

[57] ABSTRACT

The invention provides the novel ruthenium carbonylate anions $[Ru_4(CO)_{11}]^{6-}$ and $[Ru_6(CO)_{17}]^{4-}$ and $[Ru_6(CO)_{16}]^{6-}$, together with the salts and acids of these anions. The former anion can be prepared by reduction of either $Ru_3(CO)_{12}$ or $[Ru_4(CO)_{12}]^{4-}$ with controlled amounts of an alkali metal in the presence of an electron carrier compound, while the latter two anions are prepared by a similar reduction of $[Ru_6(CO)_{18}]^{2-}$. $[Ru_6(CO)_{16}]^{6-}$ can also be prepared by a similar reduction of $[Ru_6(CO)_{17}]^{4-}$.

38 Claims, No Drawings

RUTHENIUM CARBONYLATES AND PROCESSES FOR THEIR PREPARATION

The government has rights in this invention pursuant to Grant CHE-79-18148 awarded by the National Science Foundation.

BACKGROUND OF THE INVENTION

This invention relates to ruthenium carbonylates and processes for their preparation. More specifically, the invention relates to the ruthenium carbonylate anions $[Ru_4(CO)_{11}]^{6-}$, $[Ru_6(CO)_{17}]^{4-}$, and $[Ru_6(CO)_{16}]^{6-}$ together with the salts and acids of these anions, and the processes for the preparation of all these compounds.

In U.S. Pat. No. 4,349,521 (which describes an invention of one of us (Sheldon G. Shore) and Colleen C. Nagel, and which is assigned to the same assignee as the present application) and in a paper by the said Sheldon G. Shore and Colleen C. Nagel in *J. Chem. Soc. Chem. Comm.*, 1980, page 530, there are described processes for the preparation of various ruthenium carbonylate anions by the controlled reduction of triruthenium dodecacarbonyl, $Ru_3(CO)_{12}$. This controlled reduction of triruthenium dodecacarbonyl is effected by treatment with a mixture of an alkali metal, an electron carrier compound able to carry an electron produced by the ionization of the alkali metal to the triruthenium dodecacarbonyl and a solvent which will solubilize the electron-bearing form of the carrier compound. As will be apparent to those skilled in the art, the actual reducing agent in such processes is the electrons produced by ionization of the alkali metal to form alkali metal cations, the electrons thus produced being transferred to the triruthenium dodecacarbonyl by the electron carrier compound. The product of the reduction reaction varies with the molar ratio of alkali metal:triruthenium dodecacarbonyl employed; at a molar ratio of 1:1, the product is $[Ru_6(CO)_{18}]^{2-}$, at a molar ratio of about 1.5:1 the product is $[Ru_4(CO)_{13}]^{2-}$, at a molar ratio of 2:1 the product is $[Ru_3(CO)_{11}]^{2-}$, and at a molar ratio of 3:1 the product is $[Ru_4(CO)_{12}]^{4-}$.

We have now discovered that if the molar ratio of alkali metal to triruthenium dodecacarbonyl in the above reaction increased at least to about 4.5:1, a novel ruthenium carbonylate anion of the formula $[Ru_4(CO)_{11}]^{6-}$ is formed; the formation of this anion is surprising because hitherto no ruthenium carbonylate anions bearing such a high charge have been known. We have also discovered that the same anion may be produced by reacting the anion $[Ru_4(CO)_{12}]^{4-}$ produced as described above with the same mixture of alkali metal, carrier compounds and solvent provided at least about 2 moles of the alkali metal are used for each mole of $[Ru_4(CO)_{12}]^{4-}$. We have also discovered that anions $[Ru_6(CO)_{17}]^{4-}$, and $[Ru_6(CO)_{16}]^{6-}$ which apparently cannot be produced directly by reduction of triruthenium dodecacarbonyl can be produced by treating $[Ru_6CO_{18}]^{2-}$ with an alkali metal, together with the electron carrier compound and solvent used in the aforementioned reactions. Finally, we have discovered that the anion $[Ru_6(CO)_{16}]^{6-}$ can also be prepared by treating $[Ru_6(CO)_{17}]^{4-}$ with an alkali metal, together with the electron carrier compound and solvent used in the aforementioned reactions.

SUMMARY OF THE INVENTION

Accordingly, this invention provides the ruthenium carbonylate anions of the formulae $[Ru_4(CO)_{11}]^{6-}$, $[Ru_6(CO)_{17}]^{4-}$ and $[Ru_6(CO)_{16}]^{6-}$ together with the salts (and more specifically the alkali metal, amine-derived, quaternary ammonium and phosphonium salts) of these anions, and the acids $H_6[Ru_4(CO)_{11}]$, $H_4[Ru_6(CO)_{17}]$ and $H_6[Ru_6(CO)_{16}]$ derived from these anions.

The invention also provides a process for preparing the ruthenium carbonylate anion of the formula $[Ru_4(CO)_{11}]^{6-}$ which comprises treating $Ru_3(CO)_{12}$ with a mixture of an alkali metal, a carrier compound which will carry an electron produced by the ionization of the alkali metal to the $Ru_3(CO)_{12}$, and a solvent which will solubilize at least the electron-bearing form of the carrier compound, each mole of the $Ru_3(CO)_{12}$ being treated with at least about 4.5 moles of the alkali metal.

The invention further provides a second process for preparing the ruthenium carbonylate anion of the formula $[Ru_4(CO)_{11}]^{6-}$ which comprises treating the anion $[Ru_4(CO)_{12}]^{4-}$ with a mixture of alkali metal, a carrier compound which will carry an electron produced by the ionization of the alkali metal to the $[Ru_4(CO)_{12}]^{4-}$, and a solvent which will solubilize at least the electron-bearing form of the carrier compound, each mole of the $[Ru_4(CO)_{12}]^{4-}$ being treated with at least about 2 moles of the alkali metal.

The invention further provides the ruthenium carbonylate anions of the formula $[Ru_6(CO)_x]^{y-}$, where $x=17$ and $y=4$ or $x=16$ and $y=6$, together with the salts (and specifically the alkali metal, amine-derived, quaternary ammonium and phosphonium salts) of these anions, and the completely protonated forms of these anions, namely $H_4[Ru_6(CO)_{17}]$ and $H_6[Ru_6(CO)_{16}]$.

The invention also provides a process for preparing the ruthenium carbonylate anions of the formula $[Ru_6(CO)_{17}]^{4-}$ and $[Ru_6(CO)_{16}]^{6-}$ which comprises treating the anion $[Ru_6(CO)_{18}]^{2-}$ with a mixture of an alkali metal, a carrier compound which will carry an electron produced by the ionization of the alkali metal to the $[Ru_6(CO)_{18}]^{2-}$, and a solvent which will solubilize at least the electron-bearing form of the carrier compound, each mole of the $[Ru_6(CO)_{18}]^{2-}$ being treated with at least about 2 moles of the alkali metal. If about 2 moles of the alkali metal are used per mole of $[Ru_6(CO)_{18}]^{2-}$ in this process, the product is $[Ru_6(CO)_{17}]^{4-}$, while if at least 4 moles of the alkali metal are used per mole of $[Ru_6(CO)_{18}]^{2-}$, the product is $[Ru_6(CO)_{16}]^{6-}$.

Finally, the invention provides a process for preparing the ruthenium carbonylate anion of the formula $[Ru_6(CO)_{16}]^{6-}$ which comprises treating the anion $[Ru_6(CO)_{17}]^{4-}$ with a mixture of an alkali metal, a carrier compound which will carry an electron produced by the ionization of the alkali metal to the $[Ru_6(CO)_{17}]^{4-}$, and a solvent which will solubilize at least the electron-bearing form of the carrier compound.

All of the instant ruthenium carbonylate anions may be converted to their completely protonated forms (i.e. the corresponding acids) by treatment with a protic acid.

DETAILED DESCRIPTION OF THE INVENTION

The preferred salts of the instant ruthenium carbonylate anions are the alkali metal and phosphonium salts, especially the sodium and tetraphenyl phosphonium salts, namely, $Na_6[Ru_4(CO)_{11}]$, $[PPh_4]_6[Ru_4(CO)_{11}]$, $Na_4[Ru_6(CO)_{17}]$, $[PPh_4]_4[Ru_6(CO)_{17}]$, $Na_6[Ru_6(CO)_{16}]$ and $[PPh_4]_6[Ru_6(CO)_{16}]$ (where Ph represents a phenyl group. Those skilled in the art will appreciate that, when the anions are produced by reduction of $Ru_3(CO)_{12}$, $[Ru_4(CO)_{12}]^{4-}$, $[Ru_6(CO)_{18}]^{2-}$ or $[Ru_6(CO)_{17}]^{4-}$ by the instant processes, the anions will be present in the form of an alkali metal salt. Salts of the anions other than alkali metal salts may conveniently be prepared from the alkali metal salts by metathesis; for example, reaction of the alkali metal salts of the anions with a phosphonium or ammonium salt will produce the corresponding phosphonium or ammonium salts of the anion. The tetraphenylphosphonium salts are conveniently prepared by reaction of an alkali metal salt of the anion with tetraphenylphosphonium bromide, acetonitrile being a convenient solvent for this reaction.

In the various reduction processes of the invention used to prepare $[Ru_4(CO)_{11}]^{6-}$, $[Ru_6(CO)_{17}]^{4-}$, and $[Ru_6(CO)_{16}]^{6-}$ the preferred alkali metals are sodium and potassium on grounds of cost, sodium being generally preferred. The carrier compounds used in these reduction processes are the same as those described in the aforementioned U.S. Pat. No. 4,349,521. Suitable electron carriers include, for example, benzophenone, naphthalene, anthracene, liquid ammonia, trimethylamine, crown ethers, cryptates and the like. The common feature of these electron carriers which permits the use in the instant reduction processes is that they remove electrons from the alkaline metal but yield them up to the ruthenium carbonyl or carbonylate substrate being treated; thus, suitable electron carriers have a greater affinity for electrons than the alkali metal but less electron affinity than the ruthenium carbonyl or carbonylate substrate. Those skilled in the art will thus have no difficulty making a proper choice of electron carrier for use in the instant processes. In general, we prefer to use benzophenone as the electron carrier. The solvent used in the instant processes may be any solvent which will solubilize at least the electron-bearing form of the carrier compound providing of course that the solvent does not destroy either the free or electron bearing form of the carrier compound or the ruthenium carbonyl or carbonylate substrate. For obvious reasons, aqueous solvents are unsuitable, but appropriate solvents include ethers, for example, dimethyl ether, diethyl ether, tetrahydrofuran and glymes, and halogenated alkanes, for example methylene chloride, hexamethyl phosphoramide and the like. Liquid ammonia and alkyl amines are also usable in the instant processes. In general, we prefer to use tetrahydrofuran as the solvent in the instant processes.

When the substrate reduced by the instant processes is the carbonylate anion $[Ru_4(CO)_{12}]^{4-}$, $[Ru_6(CO)_{18}]^{2-}$, or $[Ru_6(CO)_{17}]^{4-}$, this carbonylate anion starting material is conveniently present in the form of an alkali metal salt. Thus, where these carbonylate anion starting materials are prepared by reduction in the manners already described, the alkali metal ruthenium carbonylate salt which is produced as the direct product of the reduction reaction can be used directly in the instant processes without conversion to another salt of the anion.

The temperature at which the instant reduction reactions are carried out does not appear to be critical, provided of course that it is not so high as to cause decomposition of any of the reactants or products. The reactions tend to be slow, taking about 2-3 days at 60° C. and thus a temperature of 40°-80° C. is recommended to ensure that the reaction proceeds at a reasonable rate.

In the instant protonation reactions to produce $H_6[Ru_4(CO)_{11}]$, $H_4[Ru_6(CO)_{17}]$, and $H_6[Ru_6(CO)_{16}]$ it appears to be necessary to use a strong acid. Suitable acids include sulfuric acid, hydrochloric acid, hydrobromic acid, phosphoric acid and the like, with hydrochloric acid being generally preferred. In contrast to the instant reduction reactions, which can be carried out at elevated temperatures without decomposition of the products, the instant protonation reactions yield products which decompose rapidly at room temperature. Accordingly, the instant protonation reactions are desirably conducted at a temperature below about 0° C., and preferably below about $-50°$ C. A temperature of $-78°$ C. has been found convenient for these reactions. The reactions with the acid may be conducted in any of the aforementioned solvents, tetrahydrofuran generally being preferred as a solvent for the reactions.

Since the instant carbonylate anions and their compounds tend to be sensitive to both molecular oxygen and water, it is desirable to carry out all the instant reactions in an environment free from molecular oxygen or water. Such conditions are not difficult to provide since, at least on a laboratory scale, the instant reactions are conveniently handled by high-vacuum line techniques such as those described in Shriver, D. F., "The manipulation of air sensitive compounds,", McGraw-Hill, N.Y., (1969). Provided the instant reactions are carried out in the absence of air and water, yields are good; as described in the examples below, all the instant reduction reactions have been carried out with yields of at least 80%, while the instant metathesis and protonation reactions are essentially quantitative. Analytical and spectral data characterizing the instant novel compounds are also given in the examples below.

The instant compounds are useful as catalysts in hydroformylation and in the fixation of carbon dioxide from the gaseous state. Prior catalytic activity of transition metal carbonyl clusters is reported by Basset and Smith, Abstracts of Invited Talks, XIXth International Conference of Pure and Applied Chemistry, Prague, Czechoslovakia, pages 161-164 (1978). Additionally, the ruthenium carbonylate compounds of this invention may find use as heterogeneous catalysts by a suitable reaction with an acidic support in a manner analogous to that described by McVicker and Vannice, Exxon Research and Engineering Company, Corporate Pioneering Research Laboratories, Linden, N.J. (1979). Furthermore, the ruthenium carbonylate compounds synthesized herein may provide unusual catalytic activity by their decomposition onto a support to generate unique crystals of metallic ruthenium. The instant compounds are also likely to be useful in other catalytic activities for the reasons stated in J. M. Basset and R. U. Ugo, Chapter 2, "Structure and Electronic Relations Between Molecular Clusters and Small Particles: An Essay to the Understanding of Very Dispersed Metals", *Aspects of Homogeneous Catalysis*, Vol. 3, D. Reidel (ed.), Dordrecht, Holland (1977).

Examples of the anions, salts and acids of this invention, together with processes for their preparation will now be given though by way of illustration only.

EXAMPLE I

This example illustrates the preparation of the sodium salt of the anion $[Ru_4(CO)_{11}]^{6-}$ by reduction of triruthenium dodecacarbonyl.

Sodium metal (2.40 mmoles), benzophenone (2.40 mmoles), and triruthenium dodecacarbonyl (0.53 mmoles) were placed in a reaction vessel held under a dry nitrogen atmosphere. The vessel was evacuated and about 10 ml of dry tetrahydrofuran (THF) was condensed therein. The vessel was then thermostated at 60° C. with stirring for three days. About 1.86 mmoles of carbon monoxide (about 98% of theoretical) was evolved during the reaction. The reaction proceeded according to the following equation:

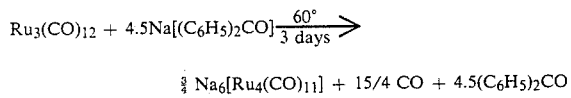

$$Ru_3(CO)_{12} + 4.5Na[(C_6H_5)_2CO] \xrightarrow[\text{3 days}]{60°}$$
$$\tfrac{2}{3} Na_6[Ru_4(CO)_{11}] + 15/4\ CO + 4.5(C_6H_5)_2CO$$

The THF was then evaporated under low pressure and 5 ml of diethyl ether was added to precipitate the crystalline sodium salt as a red-brown powder. The sodium salt isolated was heavily soluated with THF (about 6 moles of THF per mole of salt) and extremely air-sensitive, inflaming in air when in contact with tissue paper.

EXAMPLE II

This example illustrates the preparation of the same sodium salt as in example I by the reduction of the $[Ru_4(CO)_{12}]^{4-}$ anion.

Sodium metal (0.86 mmoles), benzophenone (0.86 mmoles) and $Na_4[Ru_4(CO)_{12}]$ (0.43 mmoles) were placed in a reaction vessel held under a nitrogen atmosphere. The vessel was evacuated and about 10 ml of dry THF was condensed therein. The vessel was thermostated at 60° C. and left under stirring for three days. About 0.34 mmoles of CO (about 80% of theoretical) was evolved from the vessel during the reaction, which proceeded according to the following equation:

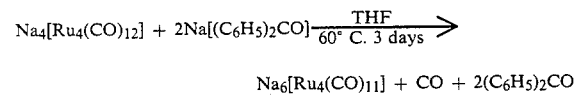

$$Na_4[Ru_4(CO)_{12}] + 2Na[(C_6H_5)_2CO] \xrightarrow[\text{60° C. 3 days}]{THF}$$
$$Na_6[Ru_4(CO)_{11}] + CO + 2(C_6H_5)_2CO$$

The THF was evaporated under reduced pressure and 5 ml of diethyl ether added to precipitate $Na_6[Ru_4(CO)_{11}]\cdot(THF)_6$ as a red-brown powder in 80% yield.

Elemental analysis yielded the following results: Calculated: C, 32.76; H, 3.77; Na, 10.75; Ru, 31.51. Found: C, 33.6; H, 1.92; Na, 10.28; Ru 31.93.

The infrared spectrum of this salt in solution in THF at ambient temperature showed bands at 1940 (medium, shoulder), 1906 (strong) and 1690 (medium, broad) $cm^{-1}$. The $^{13}C$ nuclear magnetic resonance spectrum of the sodium salt in THF-$d_{-8}$ were recorded at 25° C. and −90° C., but even at the latter temperature the slow exchange limit had not been reached. At 25° C., the salt showed a single sharp resonance at 234 ppm., while at −90° C. three resonances were observed at 228, 217 and 211 ppm., these peaks lying in the range expected for terminal carbon monoxides. Also at −90° C., small peaks had begun to rise from the baseline in the region of 279–295 ppm., these peaks possibly being due to bridging carbonyl (cf. Todd, L. P. J. et al, *J. Organomet. Chem.*, 77, 1(1974)).

EXAMPLE III

This example illustrates the conversion of the sodium salt of $[Ru_4(CO)_{11}]^{6-}$ to the tetraphenylphosphonium salt of the anion.

100 mg. of the sodium salt prepared in Example II above was dissolved in 5 ml of acetonitrile and mixed with a solution of 253 mg of tetraphenylphosphonium bromide in 5 ml of acetonitrile. Sodium bromide precipitated out leaving a solution of $[PPh_4]_6[Ru_4(CO)_{11}]$. Conductivity measurements on this compound in acetonitrile at room temperature gave a value of 764 $ohm^{-1}cm^{-2}mole^{-1}$, which is in good agreement with the accepted values for 6:1 electrolytes, as set forth, for example, in Geary, W. J., *Coord. Chem. Rev.* 7, 81 (1977) and Quagliano, J. V. et al, *Inorg. Chem.*, 3, 1557(1964). The infrared spectrum of the tetraphenyl phosphonium salt in acetonitrile with ambient temperature showed bands at 1940 (medium, shoulder), 1910 (strong, broad) and 1710 (medium, broad) $cm^{-1}$, thus indicating the presence of both terminal and briding carbonyl groups.

Elemental analysis yielded the following results: Calculated for $[PPh_4]_6[Ru_4(CO)_{11}]$: C, 67.73; H, 4.60; P, 6.76; Ru, 14.71. Found C, 66.36; H, 4.65; P, 6.47; Ru, 14.63.

EXAMPLE IV

This example illustrates the preparation of $H_6[Ru_4(CO)_{11}]$.

215 mg. of the sodium salt prepared in example II above were reacted with six equivalents of hydrogen chloride in THF at −78° C. The solution rapidly changed color from brown (with a bluish tinge) to red-brown and sodium chloride precipitated. The solution of $H_6[Ru_4(CO)_{11}]$ formed was apparently stable at −78° C., but upon warming to room temperature the solution evolved 1 mole of carbon dioxide and 1 mole of hydrogen per mole of $[Ru_4(CO)_{11}]^{6-}$. Infrared analysis of the decomposition product showed the major components to be $H_4Ru_4(CO)_{12}$ and $Ru_3(CO)_{12}$.

EXAMPLE V

This example illustrates the preparation of the hexanuclear anion $[Ru_6(CO)_{17}]^{4-}$ by reduction of the isoelectronic anion $[Ru_6(CO)_{18}]^{2-}$.

Sodium metal (0.74 mmoles), benzophenone (0.74 mmoles), and disodium hexaruthenium octadecacarbonylate (0.37 mmoles) were placed in a reaction vessel held under a dry nitrogen atmosphere. The vessel was evacuated and about 10 ml. of dry tetrahydrofuran was condensed therein. The vessel was thermostated and stirred at 60° C. for two days. About 0.37 mmoles of CO (about 100% of theoretical) was evolved from the vessel during the reaction which proceeded according to the equation:

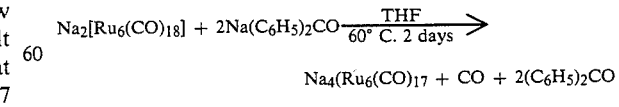

$$Na_2[Ru_6(CO)_{18}] + 2Na(C_6H_5)_2CO \xrightarrow[\text{60° C. 2 days}]{THF}$$
$$Na_4(Ru_6(CO)_{17} + CO + 2(C_6H_5)_2CO$$

The resultant sodium salt was precipitated from the THF solution by addition of hexane and dried to yield a powder. In THF solution at room temperature, the infrared spectrum of this salt showed bands at 1948 (medium, shoulder), 1930 (strong), 1860 (medium) and 1608 (broad) $cm.^{-1}$. The $^{13}C$ NMR spectrum of the salt in THF-d8 at room temperature showed a single sharp resonance at 228.7 ppm, while at −50° C., three resonances at 228.7, 218.6 and 212.0 ppm and a signal just emerging from the baseline at 279 ppm were observed.

The potassium salt of $[Ru_6(CO)_{17}]^{4-}$ was prepared in exactly the same manner from $K_2[Ru_6(CO)_{18}]$ using potassium metal as the reducing agent. However, in this case the addition of hexane was not necessary since the potassium salt of $[Ru_6(CO)_{17}]^{4-}$ is insoluble in THF and precipitated out during the course of the reaction. The infrared spectrum of the potassium salt in Nujol mull at room temperature showed bands at 1933 (strong), 1910 (strong), 1890 (strong), 1860 (medium), 1825 (medium), 1675 (very weak), 1618 (weak) and 1582 (?) cm$^{-1}$. Elemental analysis of the potassium salt, which crystallizes with 1 mole of THF, gave the following results:

Calculated for: $K_4[Ru_6(CO)_{17}]$.THF: C, 19.24; H, 0.61; K, 11.93; Ru, 46.25. Found: C, 20.69; H, 1.03; K, 12.62; Ru, 45.08.

If the quantities of alkali metal and benzophenone used in the above process are doubled, the product is the corresponding alkali metal salt of $[Ru_6(CO)_{16}]^{6-}$.

EXAMPLE VI

This example illustrates the preparation of the tetraphenylphosphonium salt of the anion $[Ru_6(CO)_{17}]^{4-}$.

170 mg. of the sodium salt prepared in Example V above was dissolved in 5 ml. of THF and treated with a stoichiometric amount of tetraphenylphosphonium bromide in tetrahydrofuran, resulting in the immediate precipitation of the tetraphenylphosphonium salt $[PPh_4]_4[Ru_6(CO)_{17}]$, which was dried under reduced pressure. This tetraphenylphosphonium salt was found to be soluble in methylene chloride and acetonitrile, but insoluble in THF, hexane and diethyl ether. Elemental analysis gave the following results:

Calculated for $[PPh_4]_4[Ru_6(CO)_{17}]$: C, 55.62; H, 3.30; P, 5.08; Ru, 24.85. Found: C, 55.49; H, 3.64; P, 4.98; Ru, 24.34.

Measurements of the conductivity of this compound in acetonitrile gave a conductivity at infinite dilution of 514 ohm$^{-1}$cm$^{-2}$mole$^{-1}$, in good agreement with the accepted value for a 4:1 electrolyte. The infrared spectrum in $CH_2Cl_2$ at room temperature showed bands and 1970 (strong), 1955 (medium, shoulder), 1750 (weak) 1660 (very weak) and 1590 (weak, broad) cm$^{-1}$. These bands reveal the presence of both terminal and briding carbonyl groups on the anion.

EXAMPLE VII

This example illustrates the preparation of $H_4[Ru_6(CO)_{17}]$.

The potassium salt prepared in Example V above was treated with four equivalents of hydrogen chloride in tetrahydrofuran under the same conditions as in Example IV above thereby precipitating sodium chloride and forming $H_4[Ru_6(CO)_{17}]$. Upon warming to room temperature, 1 mole of hydrogen was evolved for each mole of the salt and analysis of the decomposition products showed the major product to be triruthenium-dodecacarbonyl.

Precisely similar results were obtained by treating the sodium salt prepared in Example V above with hydrogen chloride under the same conditions.

EXAMPLE VIII

This example illustrates the preparation of the sodium salt of the anion $[Ru_6(CO)_{16}]^{6-}$.

154 mg. (0.131 mmole) of the sodium salt prepared in Example V above and 68.6 mg. (0.287 mmole) of $Na[(C_6H_5)_2CO]$ were placed in a reaction vessel equipped with a stir bar and an adaptor. The reaction vessel was then evacuated and approximately 5 ml. of tetrahydrofuran was distilled into the vessel. The vessel was then placed in an oil bath and heated to 60° C. for 48 hours with constant stirring. At the end of this time, a red precipitate was present in the reaction vessel and the supernatant solution was transparent light blue. The reaction vessel was immersed in liquid nitrogen and the gas evolved in the reaction vessel was collected and analyzed, being found to contain 5% of hydrogen and 95% of carbon monoxide; the yield of gas was 92% of the theoretical. After removal of the evolved gas, the reaction vessel was attached to an extractor in a nitrogen filled glove box, evacuated and the solution filtered. The precipitate was washed repeatedly with tetrahydrofuran and then with diethyl ether and dried overnight under vacuum to give a yield of 100 mg. (65%) of $Na_6[Ru_6(CO)]_{16}$.

The infrared spectrum of this sodium salt in acetonitrile at room temperature showed bands at 1906 (strong), 1850 (weak, shoulder), 1718 (medium broad), 1025 (weak, broad) and 915 (very weak) cm$^{-1}$; the last two absorptions are due to tetrahydrofuran.

The sodium salt thus prepared was then converted to the corresponding tetraphenyl phosphonium salt in the same manner as Example III above. Measurements of the conductivity of the tetraphenylphosphonium salt in acetonitrile gave a conductivity at infinite dilution of 787 ohm$^{-1}$cm$^{-2}$mole$^{-1}$, in good agreement with the accepted value for a 6:1 electrolyte. The infrared spectrum of the tetraphenylphosphonium salt in acetonitrile showed bands at 1955 (weak, shoulder), 1903 (strong), 1830 (weak, shoulder) and 1720 (weak, broad) cm$^{-1}$. Elemental analysis of the tetraphenylphosphonium salt gave the following results: Calculated for $[PPh_4]_6[Ru_6(CO)_{16}]$: C, 62.17; H, 3.91; P, 6.01; Ru, 19.62. Found: C, 61.86; H, 4.21; P, 6.03; Ru, 19.75.

Treatment of the sodium salt with the stoichiometric amount of hydrochloric acid in tetrahydrofuran at −78° C. resulted in precipitation of sodium chloride with production of $H_6[Ru_6(CO)_{16}]$. At room temperature, the solution decomposed to give carbon monoxide, hydrogen and a mixture of unidentified non-volatile products.

The $^{13}C$ NMR spectrum of the tetraphenylphosphonium salt at room temperature in acetonitrile exhibited a single signal at 228.6 ppm.

It will be apparent to those skilled in the art that numerous changes and modifications can be made in the preferred embodiments of the inventions described above without departing from the scope of the invention. Accordingly, the foregoing description is to be construed in an illustrative and not in a limitative sense, the scope of the invention being defined solely by the appended claims.

We claim:

1. The ruthenium carbonylate anion of the formula $[Ru_4(CO)_{11}]^{6-}$, the alkali metal, amine, quaternary ammonium and phosphonium salts of said anion and the completely protonated form of said anion, namely $H_6[Ru_4(CO)_{11}]$.

2. A salt according to claim 1 wherein the cation of said salt is an alkali metal or phosphonium cation.

3. The salts according to claim 2 wherein said cation is sodium or tetraphenylphosphonium, namely $Na_6[Ru_4(CO)_{11}]$ and $[PPh_4]_6[Ru_4(CO)_{11}]$.

4. A process for preparing the ruthenium carbonylate anion of the formula $[Ru_4(CO)_{11}]^{6-}$ which comprises treating $Ru_3(CO)_{12}$ with a mixture of an alkali metal, a carrier compound which will carry an electron produced by the ionization of said alkali metal to said $Ru_3(CO)_{12}$, and a solvent which will solubilize at least the electron-bearing form of said carrier compound, each mole of said $Ru_3(CO)_{12}$ being treated with at least about 4.5 moles of said alkali metal, said process being carried out in an environment free from molecular oxygen and water.

5. A process according to claim 4 wherein said alkali metal is sodium.

6. A process according to claim 4 wherein said carrier compound is benzophenone.

7. A process according to claim 4 wherein said solvent is tetrahydrofuran.

8. A process according to claim 4 which is carried out at a temperature in the range of about 40° to about 80° C.

9. A process according to claim 4 wherein the $[Ru_4(CO)_{11}]^{6-}$ formed is thereafter treated with a phosphonium or ammonium salt to produce the corresponding phosphonium or ammonium salt of said $[Ru_4(CO)_{11}]^{6-}$.

10. A process according to claim 9 wherein said phosphonium salt is tetraphenylphosphonium bromide.

11. A process for preparing the ruthenium carbonylate anion of the formula $[Ru_4(CO)_{11}]^{6-}$ which comprises treating the anion $[Ru_4(CO)_{12}]^{4-}$ with a mixture of an alkali metal, a carrier compound which will carry an electron produced by the ionization of said alkali metal to said $[Ru_4(CO)_{12}]^{4-}$, and a solvent which will solubilize at least the electron-bearing form of said carrier compound, each mole of said $[Ru_4(CO)_{12}]^{4-}$ being treated with at least about 2 moles of said alkali metal, said process being carried out in an environment free from molecular oxygen and water.

12. A process according to claim 11 wherein said alkali metal is sodium.

13. A process according to claim 11 wherein said carrier compound is benzophenone.

14. A process according to claim 11 wherein said solvent is tetrahydrofuran.

15. A process according to claim 11 wherein said $[Ru_4(CO)_{12}]^{4-}$ is present as an alkali metal salt.

16. A process according to claim 11 wherein the $[Ru_4(CO)_{11}]^{6-}$ formed is thereafter treated with a phosphonium or ammonium salt to produce the corresponding phosphonium or ammonium salt of said $[Ru_4(CO)_{11}]^{6-}$.

17. A process according to claim 16 wherein said phosphonium salt is tetraphenylphosphonium bromide.

18. A hexaruthenium carbonylate anion of the formula $[Ru_6(CO)_x]^{y-}$ where $x=17$ and $y=4$ or $x=16$ and $y=6$, the alkali metal, amine, quaternary ammonium and phosphonium salts of said anion, and the completely protonated form of said anion.

19. A salt according to claim 18 wherein the cation of said salt is an alkali metal or phosphonium cation.

20. The salts according to claim 19 wherein said cation is sodium or tetraphenylphosphonium, namely $Na_4[Ru_6(CO)_{17}]$, $Na_6[Ru_6(CO)_{16}]$, $[PPh_4]_4[Ru_6(CO)_{17}]$ and $[PPh_4]_6[Ru_6(CO)_{16}]$.

21. A process for preparing a ruthenium carbonylate anion of the formula $[Ru_6(CO)_x]^{y-}$ (where $x=17$ and $y=4$ or $x=16$ and $y=6$) which comprises treating the anion $[Ru_6(CO)_{18}]^{2-}$ with a mixture of an alkali metal, a carrier compound which will carry an electron produced by the ionization of said alkali metal to said $[Ru_6(CO)_{18}]^{2-}$, and a solvent which will solubilize at least the electron-bearing form of said carrier compound, each mole of said $[Ru_6(CO)_{18}]^{2-}$ being treated with at least about 2 moles of said alkali metal, said process being carried out in an environment free from molecular oxygen and water.

22. A process according to claim 21 wherein each mole of said $[Ru_6(CO)_{18}]^{2-}$ is treated with about 2 moles of said alkali metal and the product is $[Ru_6(CO)_{17}]^{4-}$.

23. A process according to claim 21 wherein each mole of said $[Ru_6(CO)_{18}]^{2-}$ is treated with at least about 4 moles of said alkali metal and the product is $[Ru_6(CO)_{16}]^{6-}$.

24. A process according to claim 21 wherein said alkali metal is sodium or potassium.

25. A process according to claim 21 wherein said carrier compound is benzophenone.

26. A process according to claim 21 wherein said solvent is tetrahydrofuran.

27. A process according to claim 21 wherein $[Ru_6(CO)_{18}]^{2-}$ is present as an alkali metal salt.

28. A process according to claim 21 wherein said ruthenium carbonylate anion formed is thereafter treated with a phosphonium or ammonium salt to produce the corresponding phosphonium or ammonium salt of said anion.

29. A process according to claim 28 wherein said phosphonium salt is tetraphenylphosphonium bromide.

30. A process for preparing the ruthenium carbonylate anion of the formula $[Ru_6(CO)_{16}]^{6-}$ which comprises treating the anion $[Ru_6(CO)_{17}]^{4-}$ with a mixture of an alkali metal, a carrier compound which will carry an electron produced by the ionization of said alkali metal to said $[Ru_6(CO)_{17}]^{4-}$, and a solvent which will solubilize at least the electron-bearing form of said carrier compound, said process being carried out in an environment free from molecular oxygen and water.

31. A process according to claim 30 wherein said alkali metal is sodium or potassium.

32. A process according to claim 30 wherein said carrier compound is benzophenone.

33. A process according to claim 30 wherein said solvent is tetrahydrofuran.

34. A process according to claim 30 wherein $[Ru_6(CO)_{17}]^{4-}$ is present as an alkali metal salt.

35. A process for preparing a completed protonated ruthenium carbonylate anion selected from the group consisting of $H_6[Ru_4(CO)_{11}]$, $H_4[Ru_6(CO)_{17}]$ and $H_6[Ru_6(CO)_{16}]$, which process comprises treating the corresponding unprotonated anion with a protic acid, said process being carried out in the absence of molecular oxygen and water and at a temperature not greater than about 0° C.

36. A process according to claim 35 wherein said protic acid is hydrochloric acid.

37. A process according to claim 35 which is carried out in solution in tetrahydrofuran.

38. A process according to claim 35 which is carried out at a temperature not in excess of about 0° C.

* * * * *